US005637572A

United States Patent [19]
Merlini et al.

[11] Patent Number: 5,637,572
[45] Date of Patent: Jun. 10, 1997

[54] USE OF 4'-IODO-4'-DEOXYDOXORUBICIN FOR THE TREATMENT OF AMYLOIDOSIS

[75] Inventors: Giampaolo Merlini, Pavia; Luca Gianni, Milan, both of Italy

[73] Assignees: Policlinico San Matteo, Istituto Di Ricovero E Cura A Carattere Scientifico Di Diritto Pubblico, Pavia; Istituto Nazionale Per Lo Studio E La Cura Dei Tumori, Milan, both of Italy

[21] Appl. No.: 397,248
[22] PCT Filed: Jul. 29, 1994
[86] PCT No.: PCT/EP94/02511
§ 371 Date: Apr. 12, 1995
§ 102(e) Date: Apr. 12, 1995
[87] PCT Pub. No.: WO95/04538
PCT Pub. Date: Feb. 16, 1995

[30] Foreign Application Priority Data

Aug. 6, 1993 [IT] Italy ................................ MI93A1800
Mar. 31, 1994 [IT] Italy ................................ MI94A0621

[51] Int. Cl.$^6$ .................................................. A61K 31/71
[52] U.S. Cl. ........................... 514/34; 514/788; 514/789; 514/905; 536/64
[58] Field of Search ........................ 514/34, 788, 789, 514/908; 536/64

[56] References Cited

U.S. PATENT DOCUMENTS 4,438,105  3/1984  Suarato et al. ..................... 424/180

FOREIGN PATENT DOCUMENTS 1 457 295  11/1991  European Pat. Off. .

OTHER PUBLICATIONS

"Tumori", vol. 75, No. 4, pp. 358–361, Protein Kinase C Activation and Lipid Peroxidation By Doxorubicin Analogues, Gambetta et al. 1989.

"Journal of Neurochemistry", vol. 61, No. 6, Inhibition of Beta–Amyloid Production by Activation of Protein Kinase C, Gabuzda et al. 1993.

Primary Examiner—Frederick Krass
Attorney, Agent, or Firm—Oblon, Spivak, McClelland, Maier & Neustadt, P.C.

[57] ABSTRACT

The use of 4'-iodo-4'-deoxydoxorubicin and its pharmaceutically acceptable salts in the treatment of amyloidosis is described.

7 Claims, No Drawings

USE OF 4'-IODO-4'-DEOXYDOXORUBICIN FOR THE TREATMENT OF AMYLOIDOSIS

This invention relates to a new use of an already known anthracycline with antitumoral activity.

More particularly, the invention relates to a new use of 4'-iodo-4'-deoxydoxorubicin and its pharmaceutically acceptable salts in the treatment of amyloidosis.

4'-iodo-4'-deoxydoxorubicin (IDX), of formula

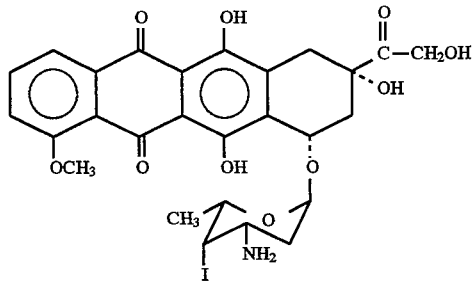

is described and claimed, together with its method of preparation, in U.S. Pat. No. 4,438,105 in the name of A. Suarato et al.

Said anthracycline, which differs from doxorubicin in that the hydroxyl in position 4' of the sugar is replaced by one atom of iodine, possesses good antitumoral activity.

The term "amyloidosis" indicates various morbid states having as their common pathological characteristic the tendency of particular proteins to polymerize and precipitate in the extracellular space in the form of insoluble fibrils, causing structural and functional damage to organs and tissues.

Although they contain a wide variety of different protein sub-units, the various types of amyloids have the same ultrastructural organization in the form of interlaced β-antiparallel sheets.

The fibrils are formed from particular light chains of monoclonal immunoglobulins and numerous other amyloidogenic proteins such as protein AA, transthyrethyne β-2-microglobulin, beta protein, which constitutes the amyloidosis of Alzheimer's disease and Down's syndrome, etc.

It has now been surprisingly found that IDX, and in particular its hydrochloride, is active in inducing degradation of amyloid fibrils.

The drug/fibril interaction is at the basis of the beneficial clinical effects observed in patients with amyloidosis. As the structure is known to be in the form of beta-parallel sheets, common to all forms of amyloidosis, 4'-iodo-4'-deoxydoxorubicin represents a reasonable hope of cure for all forms of amyloidosis and in particular for Alzheimer's disease.

Experimental Data Relative to the Linkage Between IDX and Amyloid Fibrils of Various Biochemical Compositions A predetermined quantity of amyloid fibrils (1 mg/ml) was incubated with different concentrations of IDX hydrochloride.

The incubation was conducted for 2 hours in physiological solution, the system being under constant delicate agitation.

The fibrils were then centrifuged at 5000 rpm, the optical density of the supernatant being determined at 478 nm.

The wash procedure was repeated three times.

After the final centrifuge step, the quantitative and qualitative analysis of the linkage with the fibrils was effected using a pellet.

Quantitative Analysis

The pellet was suspended in a phosphate buffer solution (PBS) and then incubated overnight with the enzyme protease. This pronase causes complete hydrolysis of the proteins.

The quantity of IDX bound to the fibrils can be measured in the supernatant by spectrophotometry at 478 nm.

The tests showed a linkage of 4±2 g of IDX per mg of fibrils.

The given data were obtained by testing the amyloid fibrils of two patients (ND and CAT) suffering from amyloidosis.

Qualitative Analysis

Qualitative analysis, conducted by immunofluorescence microscope, was effected by utilizing the spectrofluorometric properties of IDX. The following fibrils composed of:

light immunoglobulin chains (AL)
amyloid A (AA)
$\beta_2$-microglobulins (ABzM)
β-protein (AB)
transthyrethine (Var. Met 30)(ATTR) were evaluated.

The fibrils were incubated with $10^{-7}$M IDX and with DOX in 0.15M NaCl for 1 hour and washed extensively with 0.15M NaCl. The characteristic anthracycline fluorescence was evaluated by exciting at 484 nm and reading at 610 nm.

All the fibrils incubated with IDX showed intense fluorescence, whereas incubation with DOX produced no appreciable fluorescence.

Inhibition of Insulin Fibril Formation "In Vitro"

10 mg of commercial bovine insulin suspended in 1 ml $(1.74\times 10^{-3}$M) of 5% acetic acid were incubated at 85° C. for two hours until a clear gel formed. After freezing at −80° C., thawing at 37° C. and repeating this 5 times, the fibrils were centrifuged in a microcentrifuge.

IDX and DX were added in various molar ratios with respect to the fibril protein precursor (insulin). (IDX-DX:insulin; 1:2, 1:4, 1:8).

IDX but not DX completely inhibited amyloid fibril formation at molar rations of 1:1 and 1:2 and partly at a molar ratio of 1:4.

The test shows that IDX inhibits fibrilogenesis "in vitro".

Extraction of Glycosaminoglycans (GAGs) From Amyloid Fibrils and Evaluation of the Linkage With IDX The GAGs were separated from the amyloid fibrils by ion exchange chromatography in the presence of 6M urea. The method was conducted using FPLC with a Mono Q column (Pharmacia).

The fibrils were dissolved in 50 mM pH 5 phosphate buffer containing 6M urea and 0.2% CHAPS.

The separation was effected in a 0–5 molar NaCl gradient.

Using this method the fibril protein components were separated from the glycosaminoglycans (dermatan and heparan sulphate) without any irreversible denaturation occurring.

The separated protein component confirmed the high affinity for IDX observed in native fibrils.

The results of this test show that glycosaminoglycans, although being ubiquitous components of amyloid fibrils, are not necessary for the IDX linkage.

On the basis of the results obtained, IDX and its pharmaceutically acceptable salts can be advantageously used in the treatment of patients suffering from amyloidosis.

Administration is parenteral in the form of suitable injectable aqueous solutions.

Said solutions can be prepared in conventional manner in the presence of conventional supports and/or diluents (see for example the publication of L. Gianni et al. "Activity and Toxicity of 4'-iodo-4'-deoxydoxorubicin in patients with advanced breast cancer" Annals of Oncology 2: 719–725, 1991).

Dosages can vary from 5 to 150 mg/m² of body area intravenously per week. Preferably the dosage varies from 15 mg/m² to 30 mg/m² of body area intravenously per week for two-four weeks.

An essential clinical description concerning 5 patients is reported below.

Patient No. 1

This case regarded a male patient (DEP), 45 years of age, suffering from multiple myeloma (IgAλ) and amyloidosis AL with prevalent cutaneous and muscular deposition.

In July 1991 he underwent an autologous marrow transplant.

He was administered IDX at an intravenous dosage of 190 mg in 4 hours.

As early as the following morning the patient observed a considerable improvement of the skin and mobility of the limbs. During the following days urine emission of large quantities of amyloidosic protein fragments was documented together with a significant reduction in cutaneous amyloid deposits and deposits at the level of the interventricular cardiac septum (from 13 to 10 mm).

The net improvement in limb mobility and amyloid deposits persisted for the next six months without further treatment.

Patient No. 2

This case regarded a male patient (MAN) 57 years of age, suffering from amyloidosis AL (IgAλ) with prevalent involvement of the gastrointestinal tract (8–10 diarrhea discharges per day), having undergone a marked weight loss of 15 kg in six months (weight 64 kg) and with nephrotic syndrome (proteinuria 7 g/day).

He had been treated with six cycles of melphalan and prednisone completed in January 1991 without any result. In February 1992 he was treated with two doses (80 and 100 mg/m²) of IDX. In immediate post-therapy a net worsening of diarrhea, partially controlled by somatostatin (registered trademark), and of proteinuria (41 g/day) were observed, however during the subsequent months the alvus gradually improved with a net reduction in alvine discharges (3–4/day).

The patient reacquired weight (68 kg) and proteinuria settled around 4 g/day.

The general conditions of the patient improved markedly to the extent of enabling him to return to work.

Patient No. 3

This case regarded a female patient (GAB) suffering from amyloidosis (IgAλ) of mainly renal location [nephrotic syndrome with proteinuria (7 g/day)] and splenic location diagnosed in 1991.

From December 1991 to May 1992 the patient had been treated with alkylating agents without any improvement. In June the patient underwent body scintigraphy for amyloid deposits with $^{131}$I-SAP, which confirmed the renal and splenic location. In July 1992 the patient was treated with IDX at an intravenous dosage of 30 mg/m² per week for two weeks and 15 and 20 mg/m² in the next two administrations.

After an initial increase, proteinuria fell to 6 g/day, this being maintained during the next six months.

Patient No. 4

This case regarded a male patient (GRO) 70 years of age, suffering from plasmacytoma and amyloidosis AL (IgGK).

The diagnosis was made in July 1991 when the patient began to complain of intense pain in the sacral region extending to the left lower limb, such as to make walking difficult. Instrument investigation showed the presence of a solid mass, of about 10 cm diameter, determining lysis of the hemisacrum and of the left iliac ala, exerting an expansive effect in the pelvic cavity, penetrating into the vertebral canal and infiltrating the gluteal muscles.

A bioptic examination showed that myloidoma was present.

Between October 1991 and January 1992 the patient was subjected to 75 sessions of telecobalt therapy for a total of 50 Gy, and in March 1992 there began a chemotherapy cycle with cyclophosphamide at 500 mg/day for 5 days per month for a total of 6 cycles, without however achieving any radiographically evident reduction in the dimensions of the amyloidoma or a reduction in the pain symptomatology. In November 1992 scintigraphy for amyloid deposits was carried out with $^{131}$I-SAP, which confirmed the location of the tracer at the sacrum level.

The patient was then treated with IDX at a dosage of 30 mg/m² intravenously for two weeks and 20 mg/m² in the following two weeks, obtaining an almost immediate reduction in the pain symptomatology such as to induce him to interrupt the intake of analgesics.

An ultrasound diagnosis effected in January 1993 showed a reduction in the mass infiltrating the gluteals (from 12 cm to 5 cm), while magnetic resonance on the pelvis showed a reduction in the diameter of the amyloidoma from about 10 to 8 cm.

The improvement in pain symptomatology persists 14 months after treatment with IDX. Scintigraphy for amyloid deposits carried out with $^{131}$I-SAP one month after treatment with IDX and 14 months later showed gradual but complete resolution of the amyloid deposits.

Patient No. 5

This case regarded a male patient (LUS) 48 yeas of age, suffering from amyloidosis AL (CLLλ) of mainly renal and splenic location. The disorder began in September 1992 with the appearance of declive edemas. Biohumoral examinations showed the presence of massive proteinuria (12.6 g/day), dyslipemia and electrophoretic seroprotein symptoms compatible with nephrotic syndrome.

During September the patient was subjected to an echo-guided renal biopsy which showed the presence of amyloid accumulations at the level of the glomeruli and interstitial vessels. Treatment with corticosteroids began but was interrupted after a short time as it was ineffective. In January 1993 the patient underwent scintigraphy for amyloid deposits with $^{131}$I-SAP, which showed marked accumulation of the tracer at the spleen and kidney levels.

During February the patient underwent intravenous treatment with IDX at a dosage of 30 mg/m² for a total of 4 administrations.

By March 1993 the declive edemas had clearly reduced, the daily proteinuria was measured at around 6 g/day and an ultrasound check showed that the spleen dimensions had reduced from 12.3 cm (longitudinal diameter) to 11.3 cm.

We claim:

1. A method for treating amyloidosis, comprising administering to a patient in whom treatment for amyloidosis is desired a therapeutically effective quantity of 4'-iodo-4'-deoxydoxorubicin or a pharmaceutically acceptable salt thereof.

2. The method of claim 1, wherein the amyloidosis is associated with Alzheimer's disease.

3. The method of claim 1, wherein the amyloidosis is associated with Down's syndrome.

4. The method according to claim 1, wherein the 4'-iodo-4'-deoxydoxorubicin is administered intravenously to the patient at a weekly dosage varying from 15 mg/m² to 30 mg/m² of body area, in a pharmaceutically acceptable carrier, for a period of two to four weeks.

5. The method according to claim 3, wherein the 4'-iodo-4'-deoxydoxorubicin is administered intravenously to the patient at a weekly dosage varying from 15 mg/m$^2$ to 30 mg/m$^2$ of body area, in a pharmaceutically acceptable carrier, for a period of two to four weeks.

6. The method according to claim 3, wherein the 4'-iodo-4'-deoxydoxorubicin is administered intravenously to the patient at a weekly dosage varying from 15 mg/m$^2$ to 30 mg/m$^2$ of body area, in a pharmaceutically acceptable carrier, for a period of two to four weeks.

7. The method of claim 1, wherein the amyloidosis is amyloidosis AL.

* * * * *